United States Patent [19]

Muller

[11] Patent Number: 5,441,512

[45] Date of Patent: * Aug. 15, 1995

[54] HIGH INCISION VELOCITY VIBRATING SCALPEL STRUCTURE AND METHOD

[76] Inventor: George H. Muller, Apt. 508 M2, 1945 Gulf of Mexico Dr., Longboat Key, Fla. 34228

[*] Notice: The portion of the term of this patent subsequent to Apr. 26, 2011 has been disclaimed.

[21] Appl. No.: 102,849

[22] Filed: Aug. 6, 1993

Related U.S. Application Data

[63] Continuation-in-part of Ser. No. 756,422, Sep. 9, 1991, Pat. No. 5,306,282, which is a continuation-in-part of Ser. No. 023,765, dated Mar. 9, 1987, now abandoned, which is continuation-in-part of Ser. No. 422,847, now U.S. Patent 4,791,928 dated Sept. 24, 1982.

[51] Int. Cl.$^6$ .............................................. A61B 17/32
[52] U.S. Cl. ............................. 606/169; 606/171
[58] Field of Search ............... 606/169, 171, 174, 751; 30/44, 45

[56] References Cited

U.S. PATENT DOCUMENTS

| | | | |
|---|---|---|---|
| 1,552,455 | 9/1925 | Shaler | 606/169 |
| 2,100,319 | 11/1937 | Brown et al. | 606/169 |
| 4,210,146 | 7/1980 | Banko | 606/171 |
| 4,744,144 | 5/1988 | Lowery, Sr. et al. | 30/45 |
| 5,007,169 | 4/1991 | Motta | 30/45 |
| 5,214,851 | 6/1993 | Althaus | 30/44 |
| 5,243,997 | 9/1993 | Uflaker et al. | 606/169 |
| 5,306,282 | 4/1994 | Muller . | |

FOREIGN PATENT DOCUMENTS

| | | | |
|---|---|---|---|
| 4090751 | 3/1992 | Japan | 606/169 |
| 8704610 | 8/1987 | WIPO | 606/171 |

*Primary Examiner*—Edgar S. Burr
*Assistant Examiner*—John S. Hilten

[57] ABSTRACT

High incision velocity vibrating scalpel structure and method comprising motor means including a motor having a drive shaft rotatable on energizing the motor, an eccentric fly wheel secured to the drive shaft for rotation therewith and scalpel blade support structure rigidly secured to the motor, all resiliently mounted in an elongated hollow body member, to which motor means a scalpel blade may be secured and vibrated on energizing of the motor means to rotate the fly wheel and alternating or direct current means for selectively energizing the motor. A resilient pivot may also be provided for the motor means and a resilient boot is provided over one end of the body member between the body member and motor means for sealing the one end of the body member. In use, on energizing the motor means, the motor means, scalpel blade support structure and scalpel blade are caused to vibrate at a high velocity to incise tissue with the scalpel blade. Movement of the scalpel blade is primarily arcuately about the pivot mounting for the motor means, and thus is primarily perpendicularly to the axis of rotation of the drive shaft, to a lesser extent longitudinally of the high incision velocity scalpel structure.

20 Claims, 1 Drawing Sheet

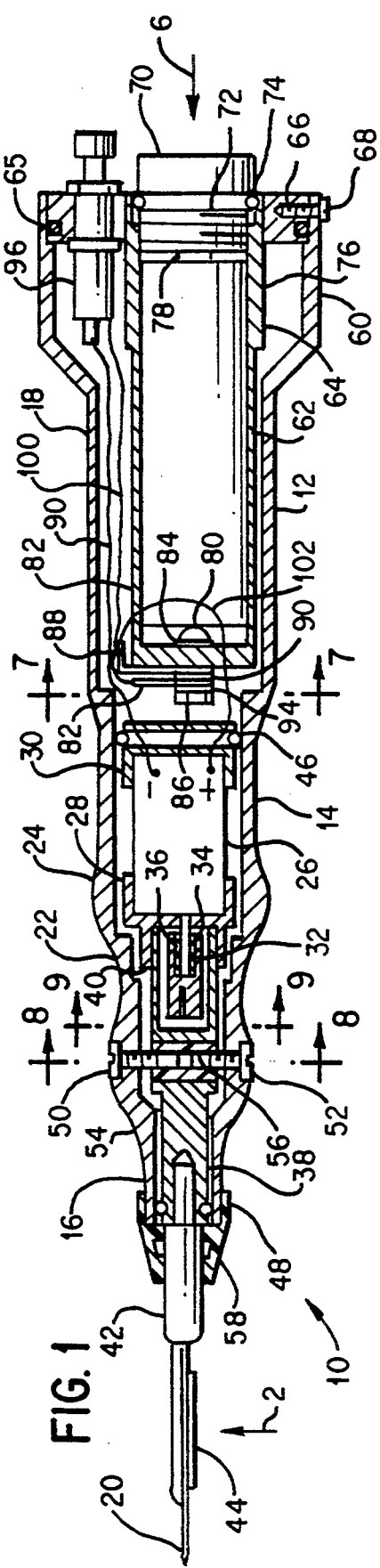
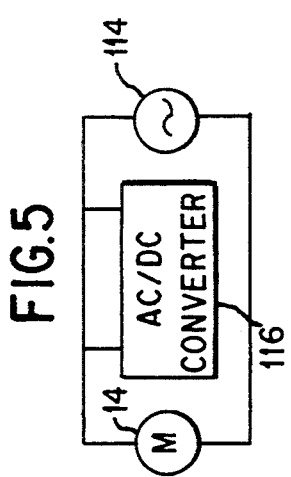
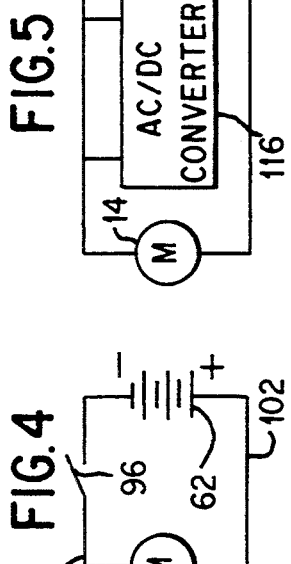
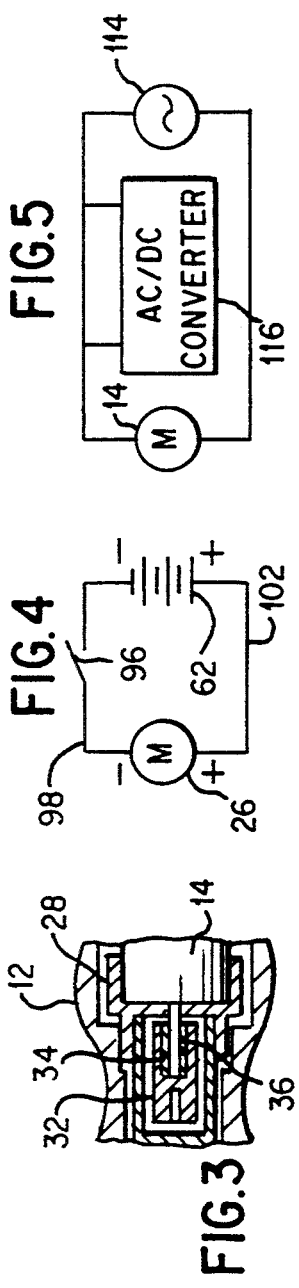
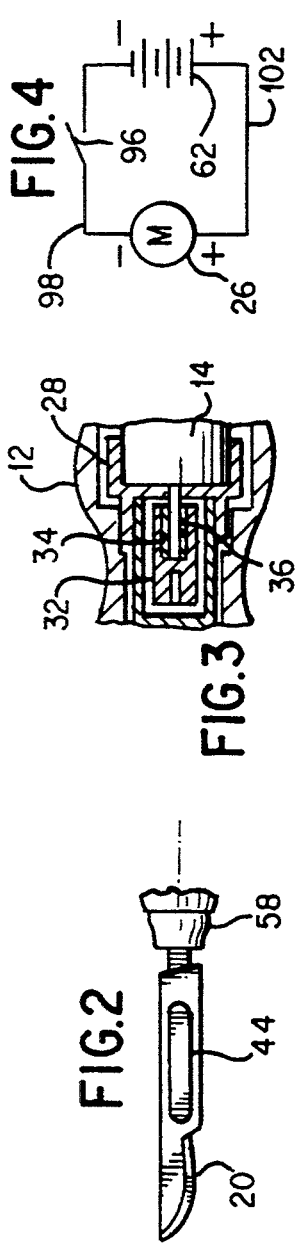
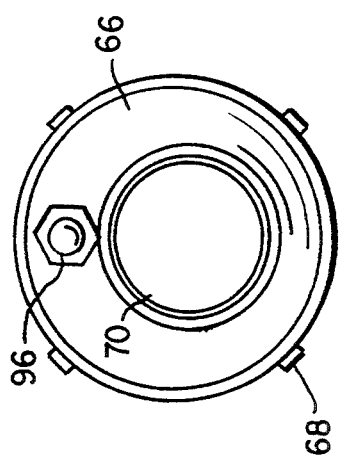
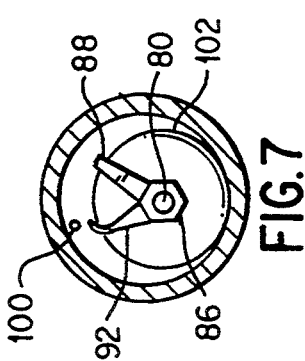
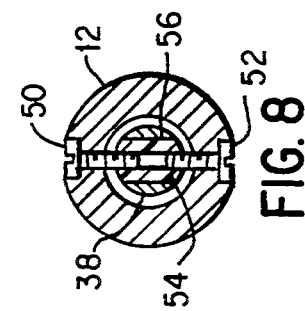
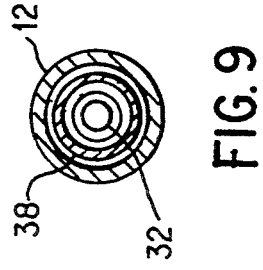

HIGH INCISION VELOCITY VIBRATING SCALPEL STRUCTURE AND METHOD

CROSS REFERENCE TO RELATED APPLICATION

This application is a Continuation in Part of application, Ser. No. 757,574, filed Sep. 11, 1991, now U.S. Pat. No. 5,306,282, which is a continuation-in-part of Ser. No. 023,765, dated Mar. 9, 1987, now abandoned, which is continuation-in-part of Ser. No. 422,847, now U.S. Patent 4,791,928 dated Sept. 24, 1982.

BACKGROUND OF THE INVENTION

1. Field of the Invention

The invention relates to surgical scalpels, and refers more specifically to a high incision velocity vibrating scalpel structure and method for power driving a scalpel blade, which structure may be completely self contained so as to be useful in remote areas without local power sources and by which structure and method a conventional linear scalpel blade is vibrated at a high velocity to produce incisions in tissue which heal rapidly with little or no scar formation.

2. Description of the Prior Art

In the past, surgical scalpel have generally been elongated handles with straight scalpel blades secured to one end thereof, which have been drawn across tissue to be incised manually. One such scalpel is shown, for example, in U.S. Pat. No. 4,140,123.

More recently, it was discovered that utilizing a rotary scalpel blade and either drawing the rotary scalpel blade across tissue to be incised at a predetermined speed with the scalpel blade being rotated due only to the friction of the blade with the tissue, or driving the scalpel blade at a predetermined velocity while it is being drawn across tissue to be incised, produces incisions which heal rapidly and with substantially less scar formation than with the use of straight bladed manually actuated scalpels. Such structures and methods are disclosed, for example, in prior U.S. Pat. No. 4,791,928.

Still more recently, the present inventor has found that surgical incisions may be made in living human tissue which also heal rapidly and produce a minimum of scar tissue, utilizing conventional straight scalpel blades which are vibrated fore and aft linearly within the plane of the curved cutting edge at high velocity while being drawn across tissue to be incised. Further, unique structure for linearly vibrating a straight scalpel blade at a high incision velocity has been developed which is simpler than that required for producing rotary motion of rotary scalpel blades, producing substantially the same surgical results, which is therefore less expensive to produce for the surgical purpose.

SUMMARY OF THE INVENTION

The present invention is a high incision velocity vibrating scalpel structure and method. In use, the high incision velocity vibrating scalpel of the invention produces incisions in tissue across which the straight scalpel blade attached to the scalpel of the invention is drawn, which incisions heal rapidly with a minimum of scar formation.

The high incision velocity scalpel structure of the invention includes an elongated cylindrical handle, the exterior surface of one end of which is shaped to receive the fingers and thumb of a surgeon utilizing the scalpel. Motor means is resiliently mounted in one end of the body member and includes a motor, an eccentric, unbalanced, fly weight driven by the motor and a scalpel blade support member rigidly secured to the motor, which motor means is supported on pivot structure by the handle. Conventional means for selectively energizing the motor means is provided in the other end of the body member.

In the method of use of the high incision velocity vibrating scalpel, the motor is energized to rotate the eccentric, unbalanced, fly wheel, whereby the entire motor means including the scalpel blade support member is caused to vibrate at a high velocity on the pivot structure to produce an essentially arcuate movement of the linear scalpel blade secured to the blade support member. The scalpel blade thus moves in high velocity vibrations, mostly perpendicularly to the axis of rotation of the eccentric, unbalanced, fly wheel, and to a lesser extent longitudinally of the scalpel structure. Such high velocity vibrating movement of the linear scalpel blade produces the desired incision when the scalpel blade is drawn across tissue to be incised.

BRIEF DESCRIPTION OF THE DRAWINGS

FIG. 1, is a longitudinal section view of the high incision velocity vibrating scalpel structure of the invention for practicing the method of the invention.

FIG. 2, is a partial elevation view of the scalpel structure illustrated in FIG. 1, taken in the direction of arrow 2 in FIG. 1.

FIG. 3, is a partial longitudinal section view of modified high incision velocity vibrating scalpel structure.

FIG. 4, is a schematic diagram of the electrical circuit of the scalpel structure of the invention.

FIG. 5, is a schematic view of a modified electrical circuit for use with the scalpel structure of the invention.

FIG. 6, is an end view of the scalpel structure of the invention, taken in the direction of arrow 6 in FIG. 1.

FIG. 7, is a section view of the scalpel structure illustrated in FIG. 1, taken substantially on the line 7—7 in FIG. 1.

FIG. 8, is another section view of the scalpel structure shown in FIG. 1, taken substantially on the line 8—8 in FIG. 1.

FIG. 9, is yet another section view of the scalpel structure illustrated in FIG. 1, taken substantially on the line 9—9 in FIG. 1.

BRIEF DESCRIPTION OF THE PREFERRED EMBODIMENT

As shown best in FIG. 1, the high incision velocity vibrating scalpel structure 10 of the invention includes a body member 12, motor means 14 mounted in one end 16 of the body member 12, and means 18 at the other end 60 of the body member for selectively energizing the motor means 14.

In accordance with the method of the invention, when the motor means 14 is energized by the means 18 for energizing the motor means, the scalpel blade 20 secured to the motor means 14 is vibrated at a high velocity to produce an incision in tissue across which the scalpel structure 10 is drawn. As indicated above, the incision produced by the scalpel structure 10 heals quickly and produces minimum scar tissue.

More specifically, the body member 12 is an elongated cylindrical member which may be constructed of metal or form sustaining plastic material as desired, having a longitudinal cross section as shown in FIG. 1. The end 16 of the body member 12 is provided with smaller diameter portions 22 and larger diameter portions 24 to facilitate gripping of the scalpel structure 10 by the fingers and thumb of a surgeon.

Motor means 14 includes a direct current motor 26 rigidly held in the cylindrical motor mounting members 28 and 30, having the cross sections shown in FIG. 1. An eccentric fly wheel member 32 is resiliently mounted on the motor drive shaft 34 by bushing 36. The eccentric fly wheel member 32 is secured to the drive shaft 34 for rotation therewith and has a center of gravity which is off center with respect to the axis of rotation of the drive shaft 34, which is also the axis of rotation of the eccentric fly wheel member 32.

The fly wheel member 32 may also, or alternatively, be unbalanced in any other manner. Accordingly, the fly wheel member 32 may, by way of example only, be constructed of material having different density. The fly wheel may thus be constructed of rubber or plastic with an off center lead weight embedded therein. Alternatively, the fly wheel may be constructed of a single material with unequal, off center, voids therein. It is only essential that the fly wheel be unbalanced, or eccentric, about its axis of rotation.

A scalpel blade support member 38, which is part of the motor means, is rigidly secured to the motor mounting member 28 at end 40 thereof. Coupling 42 is releasably engaged with the scalpel blade support member 38 and extends through the end 16 of the body member 12, and as shown best in FIGS. 1 and 2 includes on its outer end conventional structure 44 for securing a straight scalpel blade 20 thereto.

The structure 44 can be any structure for securing a straight scalpel blade 20 to coupling 42. No distinction is made between present or future structure for or methods of attaching linear scalpel blades acceptable by the medical community anywhere worldwide. The requirement is that the linear scalpel blade be secured to the coupling member 42.

The entire motor means 14 including the motor 26, motor mounting members 28 and 30, eccentric fly wheel member 32, scalpel blade support member 38, and coupling 42 is resiliently supported within the end 16 of the body member 12 by the resilient O rings 46 and 48 between the motor mount member 30 and the body member 12 and between the scalpel blade support member 38 and the body member 12 respectively.

The motor means 14 is further pivotally mounted in the body member 12 on the pivot screws 50 and 52 threaded between the body member 12 and extending into the bushing 54 within the opening 56 extending transversely through the scalpel blade support member 38.

The end 16 of the body member 12 is sealed by the flexible boot 58 extending between the end 16 of the body member 12 and the coupling 42 engaged with the scalpel blade support member 38. The boot 58 is again cylindrical and has the longitudinal cross section shown in FIG. 1.

The means 18 for energizing the motor means 14 at the other end 60 of the body member 12 as shown in FIG. 1 includes a direct current battery 62 positioned within a conductive housing 64 supported on the end cap 66. The end cap 66 is secured in the end 60 of the body member 12 by convenient means such as the radially extending screws 68. O ring 65 seals between the end cap 66 and end 60 of the body member. The plug 70 having a groove 72 therearound in which a sealing O ring 74 is positioned is threadedly engaged with the housing 64 at the end 76 thereof. As shown, the plug 70 makes electrical contact with the positive terminal 78 of the battery 62 and conducts electricity between the terminal 78 and the housing 64, as will be seen subsequently in the consideration of the circuit diagram of FIG. 4.

A negative terminal contact member 80 is supported in the end 82 of the housing 64 by the insulating and centering member 84. Contact 80 makes electrical contact with the bottom of the case of the battery 62, which is the negative terminal of the battery. Negative contact 80 is held in position in the end of the housing 64 by the nut 86. In order, the positive contact 88, insulating washer 90, negative contact 92 and conducting washer 94 are sandwiched between the end 82 of housing 64 and the nut 86, as shown best in FIG. 1.

The sealed switch 96 as shown extends through the end cap 66 and permits selective energizing of the motor 26 by the battery 62. Thus, as shown in FIG. 4, on closing of the switch 96, the motor 26 is energized by the battery 62. Referring to FIG. 1, the conductor 98 passes current from the motor 26 to the switch 96, conductor 100 passes current between the switch 96 and the battery 62 and conductor 102 passes current between the other side of the battery 62 and the other side of the motor 26.

The sealed switch 96 as well as the other seals, i.e. O rings 48, 65 and 74 and flexible boot 58 permit the high incision velocity vibrating scalpel structure 10 to be sterilized with liquid rather than gas or other non liquid methods as may be required in remote locations where only liquid sterilization may be available. Thus the structure of the invention may be sterilized by all known acceptable methods, which may be chosen in accordance with availability.

The method of operation of the scalpel structure 10 is as follows. With the straight scalpel blade 20 secured to the coupling 42 on the blade support member 38, the switch 96 is closed to energize the motor 26 from the battery 62. The motor 26 produces rotation of the drive shaft 34, which in turn rotates the eccentric fly wheel 32. Rotation of the eccentric fly wheel 32 produces a vibration of the motor means 14 including the motor 26, the blade support member 38 and the coupling 42 about the pivot screws 50 and 52 due to the resilient support of the motor means 14 by the O rings 46 and 48. Accordingly, the scalpel blade 20 is moved arcuately about the pivot screws 50 and 52 so that the principal movement of the blade 20 is perpendicular to the axis of rotation of the drive shaft 34 as shown in FIG. 1, which is the axis of generation of the body member 12. There is, then, a movement of the blade 20 perpendicular to the longitudinal axis of the scalpel structure. There is also a secondary smaller movement of the blade 20 longitudinally of the scalpel structure.

In accordance with the invention, due to the resilient support of the motor means 14, the movement of the scalpel blade 20 is substantially unaffected by the rigidity of the grip of the scalpel structure 10 by the surgeon. This is contrary to prior structures wherein the vibration was effected due to the resiliency of the surgeon's hand and varied with the tightness of his grip. The resilient mounting of the motor means 14 in accordance with the present invention is therefore a much more controlled flexible mounting, that is to say, it is substantially the same for all surgeons regardless of their strength or grip. Accordingly, more uniform incisions may be effected with the high incision velocity vibrating scalpel structure of the invention.

While one embodiment of the present invention has been considered in detail, it will be understood that other embodiments and modifications thereof are contemplated.

Thus, for example, as shown in FIG. 3, the drive shaft of the motor 14 may be bent at an angle of approximately 1° to the longitudinal axis of the scalpel structure whereby the eccentricity or unbalance of the eccentric fly wheel is accentuated to produce higher amplitude vibrations.

Also, the motor 14 shown in FIG. 1 may be energized by any available D.C. source of electricity having the required size and power output. This battery 62 may be a pair of AA batteries energizing an off the shelf motor 26, as shown. Alternatively, if a slimmer scalpel 10 is desired, the power may be from three AAA batteries and a motor selected or designed to be compatible with such D.C. power source.

Further, as shown in FIG. 5, the motor 14 may be energized from an alternating current electrical source 114, as for example a 115 volt wall socket, through an alternating current to direct current converter 116.

It is the intention to include all such embodiments and modifications such as are defined by the appended claims within the scope of the invention.

I claim:

1. Scalpel structure comprising a body member, motor means within the body members, said motor means having a longitudinal axis and including a motor, a scalpel blade support structure rigidly secured to the motor, a substantially flat scalpel blade rigidly secured to the scalpel blade support structure, said blade support structure extending exteriorly of the body member and having a longitudinal axis parallel to a longitudinal axis of the body member, means for vibrating the motor means on energizing the motor, said means for vibrating being connected to the motor means, pivot means including a fixed pivot axis extending perpendicularly of the longitudinal axis of the motor means, said pivot means pivotally supporting the motor means from the body member for reciprocating pivotal movement of the motor means and scalpel blade in the plane of the scalpel blade and in a plane perpendicular to the axis of the pivot means on energizing the motor, and means connected to the motor for energizing the motor.

2. Structure as set forth in claim 1 wherein the means for vibrating the motor means includes a rotationally unbalanced weight having an axis of rotation connected to the motor for rotation on energization of the motor.

3. Structure as set forth in claim 2 wherein the rotationally unbalanced weight is an eccentrically mounted fly wheel.

4. Structure as set forth in claim 2 wherein the rotationally unbalanced weight is constructed of material having separate portions of different density.

5. Structure as set forth in claim 2 wherein the rotationally unbalanced weight is not symmetrical about its axis of rotation.

6. Structure as set forth in claim 2 and further including resilient means operably associated with the motor means and body member for resiliently mounting the motor means in the body member.

7. Structure as set forth in claim 2 wherein the means for energizing the motor is a source of direct current electrical energy.

8. Structure as set forth in claim 2 wherein the means for energizing the motor includes a source of alternating current electrical energy.

9. Structure as set forth in claim 2, wherein the motor is a rotary motor.

10. Structure as set forth in claim 2, wherein the pivot means is a cylindrical structure having an axis of generation and extends into the body member on the axis of generation, perpendicular to the longitudinal axis of the body member and motor means, and further including a cylindrical passage through the motor means perpendicular to the longitudinal axis of the motor means receiving the cylindrical structure for rotation relative to the body member on the axis of the cylindrical structure on energizing of the motor means.

11. Structure as set forth in claim 10, wherein the cylindrical structure is two threaded cylindrical pins extending through the body member from opposite sides and having inner end portions which are unthreaded extending within the cylindrical passage through the motor means on which the motor means pivots.

12. Structure as set forth in claim 2 and further including resilient means between the motor means and pivot means, resiliently mounting the motor means on the pivot means.

13. Structure as set forth in claim 2 and further including a seal between the body member and the part of the scalpel blade support structure extending out of the body member.

14. Vibrating scalpel structure comprising an elongated hollow body member having a longitudinal axis, elongated motor means within the body member having a longitudinal axis substantially congruent with the longitudinal axis of the body member, said motor means including a motor and scalpel blade support structure rigidly secured to the motor, said support structure including a part extending out of one end of the body member, a substantially flat elongated scalpel blade, said blade rigidly secured to the scalpel blade support structure exteriorly of the one end of the body member, said blade having a longitudinally extending axis substantially congruent with the longitudinal axis of the body member and the motor means and a longitudinally extending cutting edge, means for vibrating the motor means on energizing the motor, said means for vibrating being operably connected to the motor means, pivot means having a fixed pivot axis extending perpendicularly of the longitudinal axis of the body member, motor means and scalpel blade, said pivot means pivotally supporting the motor means from the body member for arcuate reciprocating, pivotal movement of the motor means and scalpel blade in the plane of the scalpel blade in a plane perpendicular to the axis of the pivot means on energizing the motor and means connected to the motor for energizing the motor.

15. High incision velocity vibrating scalpel structure comprising an elongated hollow body member having a longitudinal axis, one end of which is adapted to fit the hand of a surgeon, elongated motor means, said motor means within the body member having a longitudinal axis substantially congruent with the longitudinal axis of the body member, and including a cylindrical passage extending therethrough perpendicular to the longitudinal axis thereof, said motor means including a rotary motor having a motor shaft and scalpel blade support structure rigidly secured to the motor, said support structure including a part extending out of the one end of the body member, a substantially flat elongated scalpel blade rigidly secured to the scalpel blade support structure exteriorly of the one end of the body member, said blade having a longitudinally extending axis substantially congruent with the longitudinal axis of the body member and the motor means and a cutting edge extending substantially parallel to the longitudinally extending axis, means for vibrating the motor means on energizing the motor connected to the motor means including a rotationally unbalanced flywheel rigidly secured to the motor shaft, pivot means having a fixed pivot axis comprising a pair of screws extending through the body member perpendicularly of the longitudinal axis of the body member, motor means and scalpel blade and into the cylindrical passage through the motor means said pivot means pivotally supporting the motor means from the body member for arcuate reciprocating pivotal movement of the motor means and scalpel blade in the plane of the scalpel blade in a plane perpendicular to the axis of the pivot means on energizing the motor, means resiliently mounting the motor means in the body member, resiliently mounting the motor means on the pivot means, means for sealing between the one end of the body member and the scalpel blade support structure, and means connected to the motor for energizing the motor.

16. The method of producing vibration of a surgical scalpel blade comprising the steps of: pivotally mounting an elongated motor means having a longitudinal axis, said motor means including a motor with means for vibrating the motor means on energizing the motor, and scalpel blade support structure, said support structure rigidly secured to the motor, within an elongated hollow body member having a longitudinal axis with the axii substantially congruent and with one end of the scalpel blade support structure extending out of one end of the body member, mounting said support structure on pivot means having a fixed pivot axis extending perpendicularly to the longitudinal axis of the body member and motor means; rigidly securing a substantially flat elongated scalpel blade having a cutting edge and a longitudinal axis to the motor means with the longitudinal axis of the scalpel blade and cutting edge extending substantially parallel to the axis of the body member and scalpel blade support member and perpendicular to the pivot axis; and energizing the motor to produce reciprocal, oscillation of the scalpel blade and motor means about the axis of the pivot means in the plane of the scalpel blade and in a plane perpendicular to the axis of the pivot means.

17. The method as set forth in claim 16 and further including the step of resiliently mounting the motor means within the body member.

18. The method as set forth in claim 16 and further including the step of resiliently mounting the motor means on the pivot means.

19. The method as set forth in claim 16 and further including the step of sealing between the one end of the body member and the one end of the scalpel blade support structure.

20. The method of producing high frequency vibrations of a surgical scalpel blade comprising the steps of: resiliently pivotally mounting an elongated motor means having a longitudinal axis, said motor means including a motor with means for vibrating the motor means on energizing the motor and scalpel blade support structure rigidly secured to the motor within an elongated hollow body member having a longitudinal axis with the axii substantially congruent and with one end of the scalpel blade support structure extending out of one end of the body member, mounting said support structure on resilient pivot means having a fixed pivot axis extending perpendicular to the longitudinal axis of the body member and motor means; rigidly securing a substantially flat, elongated scalpel blade having a cutting edge and a longitudinal axis to the motor means with the longitudinal axis of the scalpel blade and cutting edge extending substantially parallel to the axii of the body member and scalpel blade support member and perpendicular to the pivot axis; and energizing the motor to produce reciprocal, oscillation of the scalpel blade and motor means about the axis of the pivot means in the plane of the scalpel blade and in a plane perpendicular to the axis of the pivot means and sealing between the one end of the body member and the one end of the scalpel blade support structure.

* * * * *